United States Patent
Xu et al.

(10) Patent No.: US 9,081,822 B2
(45) Date of Patent: Jul. 14, 2015

(54) DISCRIMINATIVE DISTANCE WEIGHTING FOR CONTENT-BASED RETRIEVAL OF DIGITAL PATHOLOGY IMAGES

(71) Applicant: SONY CORPORATION, Tokyo (JP)

(72) Inventors: Xun Xu, Palo Alto, CA (US); Akira Nakamura, San Jose, CA (US); Shengyang Dai, San Jose, CA (US); Su Wang, San Jose, CA (US)

(73) Assignee: Sony Corporation, Tokyo (JP)

( * ) Notice: Subject to any disclaimer, the term of this patent is extended or adjusted under 35 U.S.C. 154(b) by 132 days.

(21) Appl. No.: 13/838,659

(22) Filed: Mar. 15, 2013

(65) Prior Publication Data

US 2014/0270496 A1    Sep. 18, 2014

(51) Int. Cl.
*G06K 9/00* (2006.01)
*G06F 17/30* (2006.01)

(52) U.S. Cl.
CPC ........ *G06F 17/3053* (2013.01); *G06K 9/00147* (2013.01)

(58) Field of Classification Search
None
See application file for complete search history.

(56) References Cited

U.S. PATENT DOCUMENTS

| 7,027,633 | B2 | 4/2006 | Foran et al. |
| 2003/0013951 | A1 | 1/2003 | Stefanescu et al. |
| 2006/0112095 | A1* | 5/2006 | Xie et al. ............................ 707/5 |
| 2007/0216709 | A1* | 9/2007 | Kojima et al. ................. 345/619 |
| 2007/0258630 | A1 | 11/2007 | Tobin et al. |
| 2010/0017389 | A1* | 1/2010 | Ogunbona et al. ................. 707/5 |
| 2012/0242817 | A1* | 9/2012 | Pan .................................. 348/77 |

OTHER PUBLICATIONS

Rahman, Md Mahmudur, Prabir Bhattacharya, and Bipin C. Desai. "A framework for medical image retrieval using machine learning and statistical similarity matching techniques with relevance feedback." Information Technology in Biomedicine, IEEE Transactions on 11.1 (2007): 58-69.*

Cox, Ingemar J., et al. "The Bayesian image retrieval system, PicHunter: theory, implementation, and psychophysical experiments." Image Processing, IEEE Transactions on 9.1 (2000): 20-37.*

* cited by examiner

*Primary Examiner* — Bhavesh Mehta
*Assistant Examiner* — Andrew Moyer
(74) *Attorney, Agent, or Firm* — Haverstock & Owens LLP

(57) ABSTRACT

Content-based retrieval of digital pathology images (DPI) is a fundamental component in an intelligent DPI processing and management system. The fundamental procedure of the retrieval is evaluating the similarity between the query image and every image in the database with some distance function, and sorting of the latter based on their distances to the query. A novel approach to optimally combine a set of existing distance functions into a stronger distance that is suitable for retrieving DPI in a way respecting human perception of image similarity is described herein.

24 Claims, 2 Drawing Sheets

DISCRIMINATIVE DISTANCE WEIGHTING FOR CONTENT-BASED RETRIEVAL OF DIGITAL PATHOLOGY IMAGES

FIELD OF THE INVENTION

The present invention relates to the field of digital pathology imaging. More specifically, the present invention relates to content-based retrieval of digital pathology images.

BACKGROUND OF THE INVENTION

Digital Pathology is an image-based information environment enabled by computer technology that allows for the management of information generated from a digital slide. Digital pathology is enabled in part by virtual microscopy, which is the practice of converting glass slides into digital slides that can be viewed, managed and analyzed.

SUMMARY OF THE INVENTION

Content-based retrieval of digital pathology images (DPI) is a fundamental component in an intelligent DPI processing and management system. The fundamental procedure of the retrieval is evaluating the similarity between the query image and every image in the database with some distance function, and sorting of the latter based on their distances to the query. A novel approach to optimally combine a set of existing distance functions into a stronger distance that is suitable for retrieving DPI in a way respecting human perception of image similarity is described herein.

In one aspect, a method of content-based retrieval of images using discriminative distance weighting programmed in a memory of a device comprises receiving a search query, comparing the search query with source images including evaluating the similarity between the search query and the source images with a weighted sum of a group of distance functions, sorting the source images based on the comparison of the search query with the source images and displaying the source images. The search query comprises a selected query image. Each comparison of the search query and a source image includes evaluating a set of distance functions, which are combined into a stronger distance that respects human perception of image similarity. The source images are sorted based on their distances to the search query. The source images are sorted in ascending order beginning with a most similar image with the nearest distance.

In another aspect, a method of learning optimal weights to combine distance functions for content-based retrieval of digital pathology images programmed in a memory of a device comprises collecting digital pathology image similarity information and computing optimal weights using the digital pathology image similarity information. Collecting comprises obtaining and storing human knowledge of determining digital pathology image similarity. The similarity information in a similarity information database comprises an ensemble of image triplets with a label provided for each of the triplets. The label is binary, indicating which pair of images is more similar. The binary labels are used to find the optimal weights to combine distance functions. The optimal weights are computed by minimizing a cost function. The optimal weights are computed using a geometric optimization algorithm.

In another aspect, an apparatus comprises a non-transitory memory for storing an application, the application for: receiving a search query, comparing the search query with source images including evaluating the similarity between the search query and the source images with a weighted sum of a group of distance functions, sorting the source images based on the comparison of the search query with the source images and displaying the source images and a processing component coupled to the memory, the processing component configured for processing the application. The search query comprises a selected query image. Each comparison of the search query and a source image includes evaluating a set of distance functions, which are combined into a stronger distance that respects human perception of image similarity. The source images are sorted based on their distances to the search query. The source images are sorted in ascending order beginning with a most similar image with the nearest distance.

In yet another aspect, an apparatus comprises a non-transitory memory for storing an application, the application for: collecting digital pathology image similarity information and computing optimal weights using the digital pathology image similarity information and a processing component coupled to the memory, the processing component configured for processing the application. Collecting comprises obtaining and storing human knowledge of determining digital pathology image similarity. The similarity information in a similarity information database comprises an ensemble of image triplets with a label provided for each of the triplets. The label is binary, indicating which pair of images is more similar. The binary labels are used to find the optimal weights to combine distance functions. The optimal weights are computed by minimizing a cost function. The optimal weights are computed using a geometric optimization algorithm.

DETAILED DESCRIPTION OF THE PREFERRED EMBODIMENT

Figure 1:
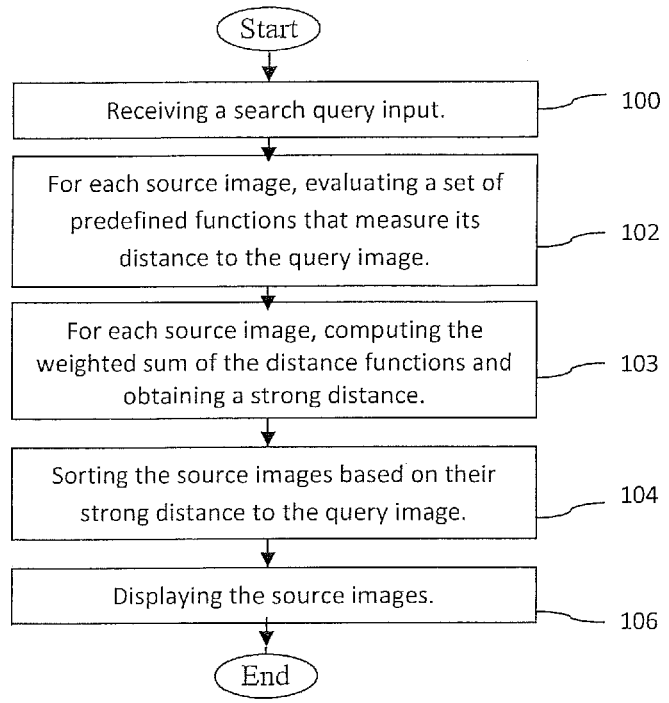
FIG. 1 illustrates a flowchart of a method of content-based retrieval of digital pathology images using discriminative distance weighting according to some embodiments.

Content-based retrieval of digital pathology images (DPI) is a fundamental component in an intelligent DPI processing and management system. The fundamental procedure of the retrieval is evaluating the similarity between the query image and every image in the database with some distance function, and sorting of the latter based on their distances to the query. A novel approach is described herein, which optimally combines a set of existing distance functions into a stronger distance that is suitable for retrieving DPI in a way respecting human perception of image similarity.

Content-based retrieval of digital pathology images (DPI) is a fundamental component in an intelligent DPI processing and management system. An important factor of content-based DPI retrieval is how to define an appropriate metric to measure image similarity, in other words, how to compute a distance between any two images. It is assumed that there are a number of ways of computing the distance between images. For example, assuming that the images are represented by feature vectors, for each individual dimension an algebraic distance is able to be computed. These component distances are able to be combined into a stronger distance that will do a better job in measuring image similarity.

One straightforward way of combining distance is adding them up. However, that would not take into consideration the relative importance of each component distance. In that way, the potentially informative component distances may submerge into uninformative distances, resulting in an inferior overall similarity metric. Naturally, finding a set of optimal weights to balance the contribution from different component distances, that will lead to a metric stronger than any component distance is of interest.

In order to quantify how good a distance is in measuring the DPI similarity, human knowledge of determining DPI similarity is collected. When a DPI database with human-labeled similarity information is possessed, determining the optimal distance weights is able to be formulated as a supervised learning problem. The formal learning procedure of the distance weights is described in the following sections.

In a DPI retrieval system, there are N source images $p_1, p_2, \ldots, p_N$ in one database, referred to as the gallery. When the user provides a query image q, the system sorts the source images according to their similarity to q and returns the first K most similar images to the user.

Retrieval is able to be formulated as a ranking problem. If a distance function D(q, p) is defined such that D is small for a similar pair (q,p), then given query q, $p_n$ is ranked based on $D(q, p_n)$ (n=1, 2, ..., N), and the first K images are returned.

It is supposed that there is a set of distance functions $d_i(\bullet,\bullet)$ (i=1, M), which are "weak" distances that are simple to compute but are not good in measuring image similarity. They are able to be combined into a stronger distance, which is able to do a better job in similarity-based ranking. Formally, a weighted sum of component distances $d_i(\bullet,\bullet)$ (i=1, ..., M) is sought:

$$D(q, p) = \sum_{i=1}^{M} w_i d_i(q, p)$$

The problem is seeking an optimal set of weights $w_i$ (i=1, ..., M).

To find the combination weights $w_i$ (i=1, ..., M), how good a distance function is able to measure image similarity is quantified. To this end, an ensemble of image triplets (q, a, b) are collected, each associated with a label $$y = \begin{cases} +1 & (q, a) \text{ is more similar than } (q, b) \\ -1 & \text{otherwise} \end{cases}$$

provided by human subjects. If (q, a) is more similar, an ideal distance function $D(\bullet,\bullet)$ should satisfy D(q,a)<D(q,b); otherwise, D(q,a)>D(q,b).

The ranking problem is able to be considered as a binary classification problem on an image triplet (q, a, b). The decision is able to be made by comparing the discriminant function:

$$L(q, a, b) = D(q, b) - D(q, a) = \sum_{i=1}^{M} w_i [d_i(q, b) - d_i(q, a)]$$

to zero. If a pseudo sample vector is defined based on the triplet:

$$\vec{x} = (q,a,b) = [d_1(q,b) - d_1(q,a), \ldots, d_M(q,b) - d_M(q,a)]$$

There is a linear classification problem on $\vec{x}$ with $$\vec{w} = [w_1, w_2, \ldots, w_M]$$

as the coefficients. In order to compute the optimal linear coefficients $\vec{w}$, an exponential cost function $$J(\vec{w}) = E\left[e^{-y\vec{w}^T\vec{x}}\right]$$

is minimized, where E[•] stands for expectation, and in practice is the average over the whole training set. This cost function measures the classification margin, implying a better generalization performance.

There are some constraints on the coefficients $\vec{w}$ to take into consideration:

As weights of distance functions, all $w_i$ (i=1, ..., M) are non-negative.

The relative importance of the component distances is what matters. To eliminate the effect of $\vec{w}$'s overall scale, its $L^2$ norm $|\vec{w}|=1$ is fixed.

As a result, a constrained optimization problem is to be solved:

$$\vec{w}^* = \operatorname*{argmin}_{\vec{w} \geq 0, |\vec{w}|=1} E\left[e^{-y\vec{w}^T\vec{x}}\right]$$

Direct solving of this problem is possible but inefficient. Considering the specific form of the constraints, a more efficient way is possible. Constraint 1 is able to be easily removed by including a logarithmic barrier, while constraint 2 is able to be considered as a manifold (hyper-sphere). Therefore, this specific constrained optimization is able to be viewed as an unconstrained optimization problem on the $|\vec{w}|=1$ manifold, and more efficient geometric optimization algorithms are able to be applied.

FIG. 1 illustrates a flowchart of a method of content-based retrieval of digital pathology images using discriminative distance weighting according to some embodiments. In the step 100, a search query is received. For example, a query image is input or selected. In the step 102, for each source image, a set of predefined functions that measure the source image distance to the query image are evaluated. In the step 103, a weighted sum of the distance functions is computed and a strong distance is obtained. The strong distance better respects human perception of image similarity. In the step 104, the source images are sorted based on the strong distance to the query image. For example, the source images are sorted in ascending order beginning with the nearest distance and ending with the farthest distance. In the step 106, the source images are displayed. In some embodiments, fewer or additional steps are implemented. In some embodiments, the order of the steps is modified.

Figure 2:
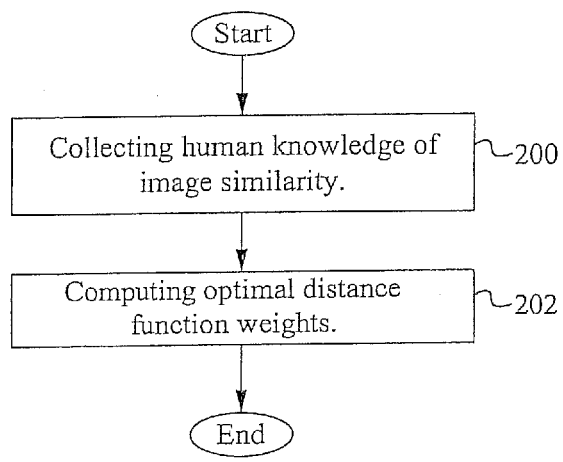
FIG. 2 illustrates a flowchart of a method of learning optimal weights to combine distance functions for content-based retrieval of digital pathology images according to some embodiments.

FIG. 2 illustrates a flowchart of a method of learning optimal weights to combine distance functions for content-based retrieval of digital pathology images according to some embodiments. In the step 200, human knowledge of determining digital pathology image similarity is collected. In some embodiments, the step 200 is skipped, and previously collected similarity information is used. In some embodiments, the collected similarity information includes an ensemble of image triplets with a label provided to each triplet by human subjects. The label indicates which source image (a or b) is closer to the query image q. In the step 202, the optimal weights to combine distance functions are found by solving a binary classification problem. The classification problem is solved by minimizing a cost function. In some embodiments, a geometric optimization algorithm is applied to minimize the cost function. In some embodiments, fewer or additional steps are implemented. In some embodiments, the order of the steps is modified.

Figure 3:
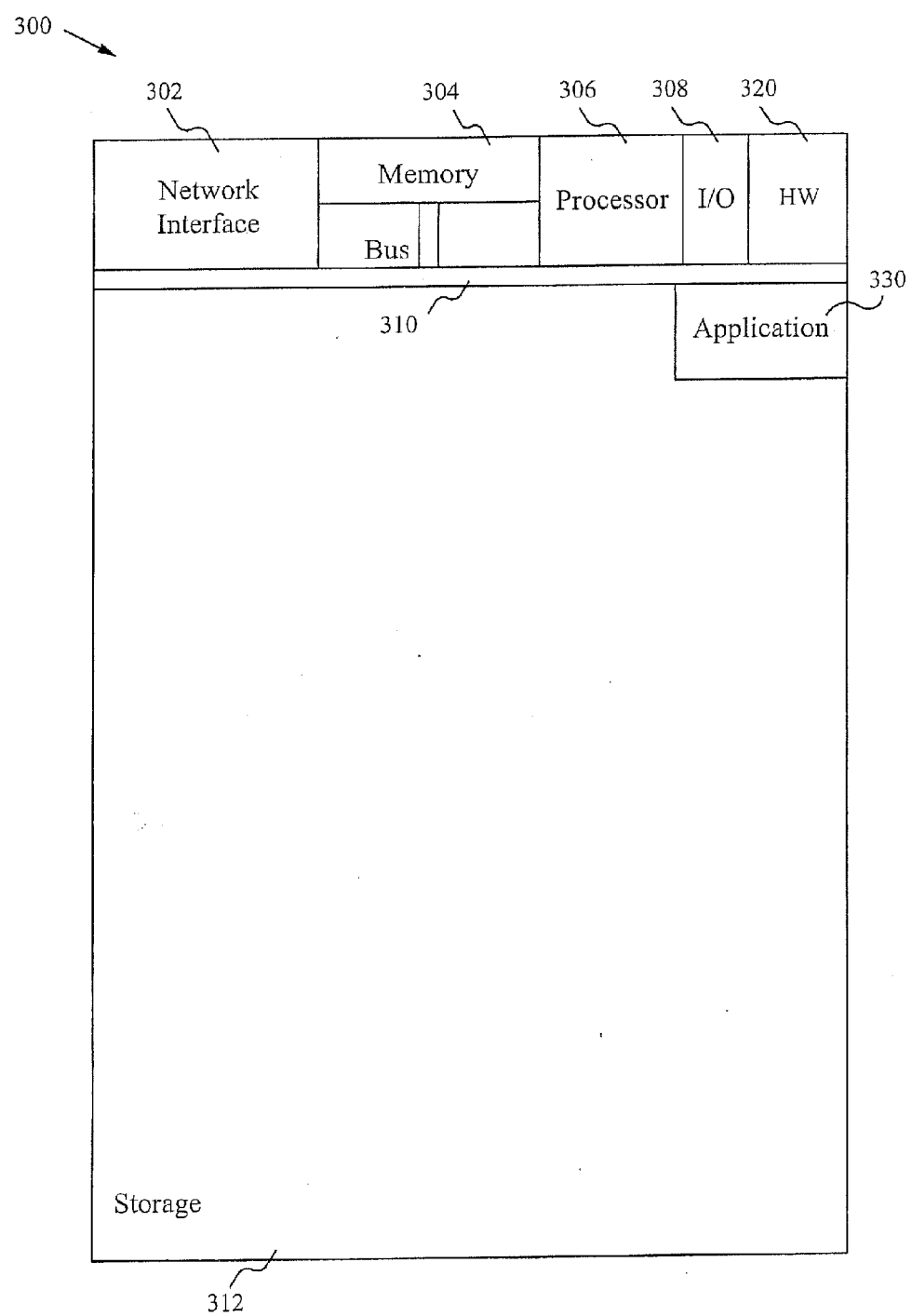
FIG. 3 illustrates a block diagram of an exemplary computing device configured to implement the content-based retrieval of digital pathology images using discriminative distance weighting method according to some embodiments.

FIG. 3 illustrates a block diagram of an exemplary computing device configured to implement the content-based retrieval of digital pathology images using discriminative distance weighting method according to some embodiments. The computing device 300 is able to be used to acquire, store, compute, process, communicate and/or display information such as text, images and videos. In general, a hardware structure suitable for implementing the computing device 300 includes a network interface 302, a memory 304, a processor 306, I/O device(s) 308, a bus 310 and a storage device 312. The choice of processor is not critical as long as a suitable processor with sufficient speed is chosen. The memory 304 is able to be any conventional computer memory known in the art. The storage device 312 is able to include a hard drive, CDROM, CDRW, DVD, DVDRW, Blu-ray®, flash memory card or any other storage device. The computing device 300 is able to include one or more network interfaces 302. An example of a network interface includes a network card connected to an Ethernet or other type of LAN. The I/O device(s) 308 are able to include one or more of the following: keyboard, mouse, monitor, screen, printer, modem, touchscreen, button interface and other devices. Content-based retrieval of digital pathology images using discriminative distance weighting application(s) 330 used to perform the content-based retrieval of digital pathology images using discriminative distance weighting method are likely to be stored in the storage device 312 and memory 304 and processed as applications are typically processed. More or less components shown in FIG. 3 are able to be included in the computing device 300. In some embodiments, content-based retrieval of digital pathology images using discriminative distance weighting hardware 320 is included. Although the computing device 300 in FIG. 3 includes applications 330 and hardware 320 for the content-based retrieval of digital pathology images using discriminative distance weighting method, the content-based retrieval of digital pathology images using discriminative distance weighting method is able to be implemented on a computing device in hardware, firmware, software or any combination thereof. For example, in some embodiments, the content-based retrieval of digital pathology images using discriminative distance weighting applications 330 are programmed in a memory and executed using a processor. In another example, in some embodiments, the content-based retrieval of digital pathology images using discriminative distance weighting hardware 320 is programmed hardware logic including gates specifically designed to implement the content-based retrieval of digital pathology images using discriminative distance weighting method.

In some embodiments, the content-based retrieval of digital pathology images using discriminative distance weighting application(s) 330 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, Blu-ray® writer/player), a television, a home entertainment system or any other suitable computing device.

To utilize the content-based retrieval of digital pathology images using discriminative distance weighting method, a device or several devices are used to search for images that are similar to a search query image. Each step is able to be performed automatically, manually or a combination thereof. The results of the search are able to include images sorted starting with a most similar image.

In operation, the described approach combines a set of component distances into a distance with stronger ranking capability. This is a flexible framework suitable for different scenarios.

Scenario 1. The component distances are able to be very weak distances, easily computed but not good in measuring image similarity. For instance, each individual distance are able to be computed from a single feature of the image.

Scenario 2. When a set of good distances has already been obtained, this framework is able to aggregate them into an even stronger one. In this sense, this approach is capable of boosting the performance of other metric learning algorithms.

The large margin formulation implies good generalization performance, e.g., making it work well on new data unseen in the training stage.

The geometric optimization technique employed is efficient, resulting in very fast algorithm training.

Some Embodiments of Discriminative Distance Weighting for Content-Based Retrieval of Digital Pathology Images 1. A method of content-based retrieval of images using discriminative distance weighting programmed in a memory of a device comprising:
   a. receiving a search query;
   b. comparing the search query with source images including evaluating the similarity between the search query and the source images with a weighted sum of a group of distance functions;
   c. sorting the source images based on the comparison of the search query with the source images; and
   d. displaying the source images.
2. The method of clause 1 wherein the search query comprises a selected query image.
3. The method of clause 1 wherein each comparison of the search query and a source image includes evaluating a set of distance functions, which are combined into a stronger distance that respects human perception of image similarity.
4. The method of clause 1 wherein the source images are sorted based on their distances to the search query.
5. The method of clause 4 wherein the source images are sorted in ascending order beginning with a most similar image with the nearest distance.
6. A method of learning optimal weights to combine distance functions for content-based retrieval of digital pathology images programmed in a memory of a device comprising:
   a. collecting digital pathology image similarity information; and
   b. computing optimal weights using the digital pathology image similarity information.

7. The method of clause 6 wherein collecting comprises obtaining and storing human knowledge of determining digital pathology image similarity.
8. The method of clause 6 wherein the similarity information in a similarity information database comprises an ensemble of image triplets with a label provided for each of the triplets.
9. The method of clause 8 wherein the label is binary, indicating which pair of images is more similar.
10. The method of clause 9 wherein the binary labels are used to find the optimal weights to combine distance functions.
11. The method of clause 6 wherein the optimal weights are computed by minimizing a cost function.
12. The method of clause 6 wherein the optimal weights are computed using a geometric optimization algorithm.
13. An apparatus comprising:
   a. a non-transitory memory for storing an application, the application for:
      i. receiving a search query;
      ii. comparing the search query with source images including evaluating the similarity between the search query and the source images with a weighted sum of a group of distance functions;
      iii. sorting the source images based on the comparison of the search query with the source images; and
      iv. displaying the source images; and
   b. a processing component coupled to the memory, the processing component configured for processing the application.
14. The apparatus of clause 13 wherein the search query comprises a selected query image.
15. The apparatus of clause 13 wherein each comparison of the search query and a source image includes evaluating a set of distance functions, which are combined into a stronger distance that respects human perception of image similarity.
16. The apparatus of clause 13 wherein the source images are sorted based on their distances to the search query.
17. The apparatus of clause 16 wherein the source images are sorted in ascending order beginning with a most similar image with the nearest distance.
18. An apparatus comprising:
   a. a non-transitory memory for storing an application, the application for:
      i. collecting digital pathology image similarity information; and
      ii. computing optimal weights using the digital pathology image similarity information; and
   b. a processing component coupled to the memory, the processing component configured for processing the application.
19. The apparatus of clause 18 wherein collecting comprises obtaining and storing human knowledge of determining digital pathology image similarity.
20. The apparatus of clause 18 wherein the similarity information in a similarity information database comprises an ensemble of image triplets with a label provided for each of the triplets.
21. The apparatus of clause 20 wherein the label is binary, indicating which pair of images is more similar.
22. The apparatus of clause 21 wherein the binary labels are used to find the optimal weights to combine distance functions.
23. The apparatus of clause 18 wherein the optimal weights are computed by minimizing a cost function.
24. The apparatus of clause 18 wherein the optimal weights are computed using a geometric optimization algorithm.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method of content-based retrieval of images using discriminative distance weighting programmed in a memory of a device comprising:
   a. receiving a search query;
   b. comparing the search query with source images including evaluating the similarity between the search query and the source images with a weighted sum of a group of distance functions, wherein the weighted sum of the group of distance function utilizes an optimal set of weights based on a database of human-labeled similarity, wherein computing the optimal weights involves constraints on coefficients, further wherein a first constraint is removed, and a second constraint is considered a hyper-sphere;
   c. sorting the source images based on the comparison of the search query with the source images; and
   d. displaying the source images.
2. The method of claim 1 wherein the search query comprises a selected query image.
3. The method of claim 1 wherein each comparison of the search query and a source image includes evaluating a set of distance functions, which are combined into a combined distance.
4. The method of claim 1 wherein the source images are sorted based on their distances to the search query.
5. The method of claim 4 wherein the source images are sorted in ascending order beginning with a most similar image with the nearest distance.
6. A method of learning optimal weights to combine distance functions for content-based retrieval of digital pathology images programmed in a memory of a device comprising:
   a. collecting digital pathology image similarity information in a database; and
   b. computing optimal weights using the database of the digital pathology image similarity information;
   c. comparing a search query with source images including evaluating the similarity between the search query and the source images with a weighted sum of a group of distance functions, wherein the weighted sum of the group of distance function utilizes the optimal weights, wherein computing the optimal weights involves constraints on coefficients, further wherein a first constraint is removed, and a second constraint is considered a hyper-sphere; and
   d. sorting the source images based on the comparison of the search query with the source images.
7. The method of claim 6 wherein collecting comprises obtaining and storing human knowledge of determining digital pathology image similarity.
8. The method of claim 6 wherein the similarity information in a similarity information database comprises an ensemble of image triplets with a label provided for each of the triplets.
9. The method of claim 8 wherein the label is binary, indicating which pair of images of the image triplet is more similar.

10. The method of claim 9 wherein the binary labels are used to find the optimal weights to combine distance functions.

11. The method of claim 6 wherein the optimal weights are computed by minimizing a cost function.

12. The method of claim 6 wherein the optimal weights are computed using a geometric optimization algorithm.

13. An apparatus comprising:
   a. a non-transitory memory for storing an application, the application for:
      i. receiving a search query;
      ii. comparing the search query with source images including evaluating the similarity between the search query and the source images with a weighted sum of a group of distance functions, wherein the weighted sum of the group of distance function utilizes an optimal set of weights based on a database of human-labeled similarity, wherein computing the optimal weights involves constraints on coefficients, further wherein a first constraint is removed, and a second constraint is considered a hyper-sphere;
      iii. sorting the source images based on the comparison of the search query with the source images; and
      iv. displaying the source images; and
   b. a processing component coupled to the memory, the processing component configured for processing the application.

14. The apparatus of claim 13 wherein the search query comprises a selected query image.

15. The apparatus of claim 13 wherein each comparison of the search query and a source image includes evaluating a set of distance functions, which are combined into a combined distance.

16. The apparatus of claim 13 wherein the source images are sorted based on their distances to the search query.

17. The apparatus of claim 16 wherein the source images are sorted in ascending order beginning with a most similar image with the nearest distance.

18. An apparatus comprising:
   a. a non-transitory memory for storing an application, the application for:
      i. collecting digital pathology image similarity information;
      ii. computing optimal weights using the digital pathology image similarity information;
      iii. comparing a search query with source images including evaluating the similarity between the search query and the source images with a weighted sum of a group of distance functions, wherein the weighted sum of the group of distance function utilizes the optimal weights, wherein computing the optimal weights involves constraints on coefficients, further wherein a first constraint is removed by including a logarithmic barrier, and a second constraint is considered a hyper-sphere; and
      iv. sorting the source images based on the comparison of the search query with the source images; and
   b. a processing component coupled to the memory, the processing component configured for processing the application.

19. The apparatus of claim 18 wherein collecting comprises obtaining and storing human knowledge of determining digital pathology image similarity.

20. The apparatus of claim 18 wherein the similarity information in a similarity information database comprises an ensemble of image triplets with a label provided for each of the triplets.

21. The apparatus of claim 20 wherein the label is binary, indicating which pair of images of the image triplet is more similar.

22. The apparatus of claim 21 wherein the binary labels are used to find the optimal weights to combine distance functions.

23. The apparatus of claim 18 wherein the optimal weights are computed by minimizing a cost function.

24. The apparatus of claim 18 wherein the optimal weights are computed using a geometric optimization algorithm.

* * * * *